(12) United States Patent
Bennett et al.

(10) Patent No.: US 10,078,089 B2
(45) Date of Patent: Sep. 18, 2018

(54) COMPOSITIONS AND METHODS FOR TREATING STEROID RESISTANT NEPHROTIC SYNDROME AND/OR STEROID SENSITIVE NEPHROTIC SYNDROME

(71) Applicant: Children's Hospital Medical Center, Cincinnati, OH (US)

(72) Inventors: Michael R. Bennett, Independence, KY (US); Prasad Devarajan, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/838,551

(22) Filed: Aug. 28, 2015

(65) Prior Publication Data

US 2016/0061845 A1 Mar. 3, 2016

Related U.S. Application Data

(60) Provisional application No. 62/043,805, filed on Aug. 29, 2014.

(51) Int. Cl.
| | | |
|---|---|---|
| *G01N 33/68* | (2006.01) | |
| *G06F 17/18* | (2006.01) | |
| *G06F 19/20* | (2011.01) | |
| *G06F 19/24* | (2011.01) | |
| *C12Q 1/6883* | (2018.01) | |

(52) U.S. Cl.
CPC ....... *G01N 33/6893* (2013.01); *C12Q 1/6883* (2013.01); *G06F 19/20* (2013.01); *G06F 19/24* (2013.01); *C12Q 2600/158* (2013.01); *G01N 2800/347* (2013.01)

(58) Field of Classification Search
None
See application file for complete search history.

(56) References Cited

PUBLICATIONS

Weigelt, et al. (2005) "Breast Cancer Metastasis: Markers and Models", Nature Reviews: Cancer, 5: 591-602.*
Caliskan, et al. (2014) "Novel Biomarkers in Glomerular Disease", Advances in Chronic Kidney Disease, 21(2): 205-16 (downloaded as NIH Public Access, 2017, 18 pages long).*
Allison, P. D., *Logistic Regression Using the SAS System: Theory and Application*, Cary, NC: SAS Institute Inc., 1999, 6 pgs.
Bagshaw, S.M., et al., "Plasma and urine neutrophil gelatinase-associated lipocalin in septic versus non-septic acute kidney injury in critical illness," Intensive care medicine, 2010, 36:452-461, 11 pgs.
Bennett, M., et al., "Urine NGAL Predicts Severity of acute Kidney Injury After Cardiac Surgery: A Prospective Study," Clin J Am Soc Nephrol, 2008, 3:665-673, 9 pgs.
Bolignano, D., et al., "Neutrophil Gelatinase-Associated Lipocalin (NGAL) and Progression of Chronic Kidney Disease," Clin J Am Soc Nephrol, 2009, 4:337-344, 8 pgs.
Bonilla-Felix, M., et al., "Changing Patterns in the Histopathology of Idiopathic Nephrotic Syndrome in Children," Kidney International, 1999, 55:1885-1890, 6 pgs.
Cattran, D.C., et al., "Long-Term Outcome in Children and Adults with Classic Focal Segmental Glomerulosclerosis," Am J Kidney Dis, 1998, 32:72-79, 8 pgs.
Cox, D. R., *The Analysis of Binary Data: Methuen's monographs on applied probability and statistics*, New York: Chapman & Hall, 1970, 3 pgs.
Cox, D. R. et al., *The Analysis of Binary Data: Monographs on Statistics and Applied Probability 32*, 2nd Edition, London: Chapman & Hall, 1989, 6 pgs.
Delong, E. R., et al., "Comparing the Areas under Two or More Correlated Receiver Operating Characteristic Curves: A Nonparametric Approach," Biometrics, 1988, 44:837-845, 10 pgs.
Eddy A.A., et al. "Nephrotic syndrome in childhood," Lancet, 2003, 362:629-639, 11 pgs.
Gipson, D.S., et al., "Differential risk of remission and ESRD in childhood FSGS," Pediatr Nephrol, 2006, 21:344-349, 7 pgs.
Gipson, D.S., et al., "Therapeutic approach to FSGS in children," Pediatr Nephrol, 2007, 22:28-36, 9 pgs.
Gipson, D.S., et al., "Management of Childhood Onset Nephrotic Syndrome," Pediatrics, 2009, 124(2):747-757, 13 pgs.
Gulati, DM, S., et al., "Changing Trends of Histopathology in Childhood Nephrotic Syndrome," Am J Kidney Dis, 1999, 34:646-650, 5 pgs.
Gulati, S, et al., "Do current recommendations for kidney biopsy in nephrotic syndrome need modifications?" Pediatric nephrology (Berlin, Germany), 2002, 17:404-408, 5 pgs.
Gygi, S.P., et al., "Quantitative analysis of complex protein mixtures using isotope-coded affinity tags," Nat Biotechnol, 1999, 17(10):994-9, 6 pgs.
Haase, MD, M., et al., "Accuracy of Neutrophil Gelatinase-Associated Lipocalin (NGAL) in Diagnosis and Prognosis in Acute Kidney Injury: A Systematic Review and Meta-analysis," Am J Kidney Dis, 2009, 54:1012-1024, 13 pgs.
Hall, I.E., et al., "IL-18 and Urinary NGAL Predict Dialysis and Graft Recovery after Kidney Transplantation," J Am Soc Nephrol., 2010, 21:189-197, 9 pgs.
Hari, P., et al., "Treatment of focal glomerulosclerosis with pulse steroids and oral cyclophosphamide," Pediatr Nephrol, 2001 16:901-905, 6 pgs.
Hirsch, R., et al., "NGAL is an early predictive biomarker of contrast-induced nephropathy in children," Pediatric Nephrology (Berlin, Germany), 2007, 22:2089-2095, 8 pgs.
Hsieh-Wilson, L.C., et al., "Lessons from the Immune System: From Catalysis to Materials Science," Acc. Chem. Res., 1996, 29:164-170, 7 pgs.
Korbet, S.M., "Clinical picture and outcome of primary focal segmental glomerulosclerosis," Nephrol Dial Transplant, 1999, 14(Suppl 3):68-73, 6 pgs.
Krawczeski, MD, C.D., et al., "Neutrophil Gelatinase-Associated Lipocalin Concentrations Predict Development of Acute Kidney Injury in Neonates and Children after Cardiopulmonary Bypass," J Pediatr, 2011, 158(6):1009-1015.e1, 8 pgs.
Mishra, J., et al., "Neutrophil gelatinase-associated lipocalin (NGAL) as a biomarker for acute renal injury after cardiac surgery," Lancet, 2005, 365:1231-1238, 8 pgs.

(Continued)

*Primary Examiner* — Robert M Kelly
(74) *Attorney, Agent, or Firm* — Frost Brown Todd LLC

(57) ABSTRACT

Disclosed are methods of determining whether a patient diagnosed with nephrotic syndrome has steroid sensitive nephrotic syndrome (SSNS) or steroid resistant nephrotic syndrome (SRNS) by determining the levels of one or more biomarkers in a biofluid from the patient. Also disclosed are methods of treating a patient diagnosed with nephrotic syndrome, and kits and substrates related to the disclosed methods.

8 Claims, No Drawings

(56) References Cited

PUBLICATIONS

Mishra, J., et al., "Identification of Neutrophil Gelatinase-Associated Lipocalin as a Novel Early Urinary Biomarker for Ischemic Renal Injury," J Am Soc Nephrol, 2003, 14:2534-2543, 10 pgs.

National Kidney Foundation, DOQI, "Clinical Practice Guidelines: For Chronic Kidney Disease: Evaluation, Classification, and Stratification," National Kidney Foundation K/DOQI, New York, NY, 2002, 356 pgs.

Peczuh, M.W., et al., "Peptide and Protein Recognition by Designed Molecules," Chem. Rev., 2000, 100:2479-2494, 16 pgs.

Roberti, I., et al., "Long-term outcome of children with steroid-resistant nephrotic syndrome treated with tacrolimus," Pediatr Nephrol, 2010, 25:1117-1124, 9 pgs.

Ross, P.L., et al., "Multiplexed Protein Quantitation in *Saccharomyces cerevisiae* Using Amine-reactive Isobaric Tagging Reagents," Mol Cell Proteomics, 2004, 3(12):1154-1169, 16 pgs.

Schwartz, G.J., et al., "New equations to estimate GFR in children with CKD," J Am Soc Nephrol, 2009, 20:629-637, 9 pgs.

Smith, J.M., et al., "Contributions of the Transplant Registry: The 2006 Annual Report of the North American Pediatric Renal Trials and Collaborative Studies (NAPRTCS)," Pediatr Transplant, 2007, 11:366-373, 9 pgs.

Srivastava, T., et al., "High incidence of focal segmental glomerulosclerosis in nephrotic syndrome of childhood," Pediatric Nephrology (Berlin, Germany), 1999, 13:13-18, 7 pgs.

Woroniecki, R.P., et al., "Urinary Proteome of Steroid-Sensitive and Steroid-Resistant Idiopathic Nephrotic Syndrome of Childhood," Am J Nephrol, 2006, 26:258-267, 11 pgs.

Woroniecki, R.P., et al., "Urinary Cytokines and Steroid Responsiveness in Idiopathic Nephrotic Syndrome of Childhood," Am J Nephrol, 2008, 28:83-90, 9 pgs.

Bennett, M., et al., "A Novel Biomarker Panel to Identify Steroid Resistance in Childhood Idiopathic Nephrotic Syndrome," Biomarker Insights, Jan. 23, 2017, 12:1-11, DOI: 10.1177/1177271917695832, 11 pgs.

\* cited by examiner

COMPOSITIONS AND METHODS FOR TREATING STEROID RESISTANT NEPHROTIC SYNDROME AND/OR STEROID SENSITIVE NEPHROTIC SYNDROME

CROSS REFERENCE TO RELATED APPLICATIONS

This application claims priority to and the benefit of U.S. Ser. No. 62/043,805, entitled "Compositions and Methods for Treating Steroid Resistant Nephrotic Syndrome and/or Steroid Sensitive Nephrotic Syndrome" filed Aug. 29, 2014, which is incorporated by reference in its entirety for all purposes.

STATEMENT REGARDING FEDERALLY SPONSORED RESEARCH OR DEVELOPMENT

This invention was made with government support under RR026314 awarded by the National Institute of Health. The government has certain rights in the invention

BACKGROUND

Idiopathic nephrotic syndrome (NS) is the most common glomerular disease in children. The two most common histopathological findings on invasive biopsy are minimal change disease (MCD) and focal segmental glomerulosclerosis (FSGS). The prognosis of children with NS depends on the underlying histopathology and can be predicted by response to steroid treatment.

Steroid resistant nephrotic syndrome (SRNS) and biopsy-proven focal segmental glomerulosclerosis (FSGS) are significantly associated with poor outcome. FSGS is a pathologic diagnosis that is steroid resistant (SRNS) in approximately 70% of cases. While total numbers of patients diagnosed with NS have remained steady, SRNS is on the rise, as marked by the increase in incidence of FSGS in children. FSGS is the most common primary glomerular disease leading to end-stage renal disease (ESRD) in children. An additional complication in patients with FSGS leading to ESRD is the high rate of recurrence (30-40%) following transplant.

An invasive renal biopsy remains the standard of diagnosis in adults. Children, however are not typically biopsied at presentation, unless they have atypical features, because response to steroids is a better predictor than histology of long term prognosis. Single renal biopsies in children tend to under diagnose FSGS, because of the focal nature of the disease, and their effectiveness in influencing outcome remains under debate.

Of the patients diagnosed with idiopathic nephrotic syndrome, over 90% of children with minimal change disease will respond to steroids and 10% will be steroid resistant. The common treatment modality for idiopathic nephrotic syndrome consists of steroids which have proved to be an adequate therapy for idiopathic nephrotic syndrome, although have remained futile in the treatment of the most common resistant forms, FSGS. Steroid responsiveness has remained the prognostic modality for the identification of FSGS in spite of invasive renal biopsies being the gold standard after failed responsive to corticosteroids [1]. Prior to the diagnosis of FSGS, all patients who present with nephrotic syndrome are presumed to have steroid-sensitive nephrotic syndrome, MCNS. Typical steroid therapy includes 2 mg/kg/day for 6-8 weeks followed by steroid taper over the course of several weeks to months and eventual discontinuation of steroids per the Ponticelli protocol[2]. This alone allows the patient to suffer possible consequences of steroid toxicity. Osteoporosis, adrenal suppression, hyperglycemia, dyslipidemia, cardiovascular disease, Cushing's syndrome, psychiatric disturbances and immunosuppression are among the more serious side effects noted with systemic corticosteroid therapy, particularly when used at high doses for prolonged periods [3]. In addition to the direct toxic side effects of steroids, patients are at risk to progressive renal injury that is only delayed by the unnecessary exposure to steroids. It has been demonstrated that if a patient has not responded to steroids by 6 months, treatment beyond this duration was not beneficial. On the other hand, management of patients with FSGS poses a therapeutic challenge, justifying the need for a more beneficial therapeutic alternative.

There are currently no diagnostic tests that accurately predict steroid responsiveness in pediatric NS or distinguish SRNS from SSNS. As such, the initial prolonged daily course of high dose corticosteroids serves both a therapeutic and diagnostic purpose. Therefore, identification of urinary biomarkers that predict steroid responsiveness or differentiate SR/FSGS from SS/MCD would benefit patients with SRNS by potentially avoiding exposure to high-dose corticosteroids.

The instant disclosure seeks to address one or more of these needs in the art.

BRIEF SUMMARY

Disclosed are methods of determining whether a patient diagnosed with nephrotic syndrome has steroid sensitive nephrotic syndrome (SSNS) or steroid resistant nephrotic syndrome (SRNS) by determining the levels of one or more biomarkers in a biofluid from the patient. Also disclosed are methods of treating a patient diagnosed with nephrotic syndrome, and kits and substrates related to the disclosed methods.

DETAILED DESCRIPTION OF THE INVENTION

As used herein, the term "biomolecule" means a biological molecule such as amino acid, peptide, protein, nucleic acid (DNA and/or RNA), lipid, carbohydrate, and their derivatives.

As used herein, the term "biomarker" means biochemicals or biomolecules (proteins, polypeptides, carbohydrates, lipids, etc, and their derivatives) associated with the presence, absence, and/or severity of specific disease states or different treatment conditions. The biomolecule may be a wild-type molecule, or a mutant, a derivative and/or a fragment thereof. For the purpose of the present invention a mutant, derivative and/or a fragment thereof means a biomolecule which possesses or share characteristics such as structure and/or biological activity similar to or which may be correlated or comparable to that of the wild type molecule. A protein or protein derivative may be used as a biomarker. Biomarkers are detectable and measurable by a variety of methods.

Expression or abundance of a biomarker may be determined from the presence or abundance of its gene, gene transcript, and gene product. The terms "gene" and "gene transcript" include RNA sequences complementary to the gene and cDNA sequences obtained by reverse transcription of the gene transcript. The terms also include the wild type gene, variations and mutations of the gene and gene transcript wherein the variation or mutation share substantial identity with the gene or gene transcript. Similarly, "gene product" includes wild type gene product, variations, fragments or derivatives thereof.

"Substantial identity" means that the variants of the gene or gene product retain sufficient identity for them to be detectable by methods and probes used for the wild type gene or gene product and retain the same functions as the wild type gene or gene products. The determination may be qualitative such as whether the biomarker is expressed, or the determination may be quantitative, or the determination may be semi-quantitative by any method known in the art such as by microarray technology, polymerase chain reaction or colorimetric method. Departure (increase or decrease) from normal levels in the non-diseased state can indicate a disease state or predisposition to a disease state. For example, the overexpression or increased abundance of a protein may be indicative of a disease state, the severity of the disease state and hence the prognosis for the subject in which the biomarker was determined, and/or it might be an indicator of susceptibility to a disease state. The difference in expression and abundance may be determined between different biomarkers or between the same biomarker under different conditions or time points. The expression of the biomarker(s) may then be compared and correlated to a reference value or to other values obtained at different time points or between different biomarkers to determine the correlation with the presence, severity of a disease state, to determine the efficacy of a treatment, or to determine a prognosis of the disease outcome for the subject. Reference values may be determined from a statistically significant number of subjects suffering from or not suffering from the disease. The expression of the biomarker(s) may also be used in conjunction with other suitable diagnostic or prognostic markers, biomarkers or indices to obtain a higher level of confidence. When a biomarker is said to be "over expressed" when compared to controls, it is meant that the expression of that biomarker is at an abundance or level that is statistically significantly more than that naturally expressed by at least one wild type or non-mutant control subject not diagnosed with the disease state or condition. Similarly, when a biomarker is "under expressed", the expression of that biomarker is statistically significantly less than that naturally expressed by at least one wild type or non-mutant control subject not diagnosed with the disease state or condition. Under this definition, a subject genetically deficient for that biomarker cannot be said to be under expressing that biomarker. Similarly, when transfected with the gene for that biomarker so that that biomarker is expressed, the deficient subject cannot be said to be over expressing the biomarker as he was originally deficient in that biomarker.

As used herein, the term "control" means a reference subject, experiment or value by which values obtained in tests can be compared against. Control values or ranges usually represent the "normal" state so that a statistically difference or deviation of the control values or ranges represents an abnormal or disease state. A person skilled in the art will know how to select and/or obtain control subjects, experiments or values for use as references.

As used herein, the term "treating" means the administration of a composition to a subject, who has a disorder as described herein, with the purpose to cure, alleviate, relieve, remedy, prevent, or ameliorate the disorder, the symptom of the disorder, the disease state secondary to the disorder, or the predisposition toward the disorder.

As used herein, the term "effective amount" is an amount of the composition that is capable of producing a medically desirable result, e.g., as described above, in a treated subject. This method can be performed alone or in conjunction with other drugs or therapy.

The term "subject" as used herein refers to any member of the animal kingdom.

"Weighted sum" means a compilation of scores from individual markers, each with a predictive value. Markers with greater predictive value contribute more to the sum. The relative value of the individual markers is derived statistically to maximize the value of a multivariable expression, using known statistical paradigms, such as logistic regression. A number of commercially available statistics packages can be used. In a formula, such as a regression equation, of additive factors, the "Weight" of each factor (marker) is revealed as the coefficient of that factor.

"Statistically significant" means differences unlikely to be related to chance alone.

"Marker" is a factor, indicator, metric, score, mathematic manipulation and the like that is evaluated and usable in a diagnosis. A marker can be, for example, a polypeptide or an antigen, or can be an antibody that binds an antigen. A marker also can be any one of a binding pair or binding partners, a binding pair or binding partners being entities with a specificity for one another, such as an antibody and antigen, hormone and receptor, a ligand and the molecule to which the ligand binds to form a complex, an enzyme and co-enzyme, an enzyme and substrate and so on.

The development of a panel of biomarkers could be used to distinguish patients with steroid resistant nephrotic syndrome (SRNS) from steroid sensitive nephrotic syndrome (SSNS). This method could directly guide therapies used to treat SRNS patients at initial disease presentation, like those with FSGS, and limit exposure to steroids that will not improve outcomes in this patient population. Furthermore, by using these biomarkers prior to eight weeks, therapies like ritixumab, calcineurin inhibitors, mycophenolate mofetil (MMF), azathioprine, cyclophosphamide and/or plasmapheresis could be initially used and thus limiting the unnecessary toxic side effects of steroids which ultimately improving outcomes for patients with this serious disease[4, 5, 6, 7, 8]. By knowing the exact type of nephrotic syndrome early in the development of disease, this patient population would have early improvement of symptoms in addition to limiting adverse reactions associated with futile therapies.

Applicant has found that, by assaying levels of various proteins (or biomarkers) in patients with nephrotic disease, the patient population may be stratified into Steroid Sensitive and Steroid Resistant patients and treated accordingly. In particular, such proteins may be measured in the urine of patients. Urinary levels of the disclosed biomarkers allow for early treatment of patients with the appropriate therapy.

Method

In one aspect, a method of treating a subject having a nephrotic syndrome is disclosed. The method may comprise the step of determining the level of one or more biomarkers in a biofluid, wherein the biomarker indicates a level of a protein selected from Vitamin D-binding protein, Alpha-2-HS-glycoprotein, Hemopexin, Transthyretin, Apolipoprotein A-I, Angiotensinogen, Complement C3, Alpha-2-macroglobulin, Alpha-1-acid glycoprotein, Thyroxine-binding globulin, Alpha-1-acid glycoprotein 2, Zinc-alpha-2-glycoprotein, Alpha-1B-glycoprotein, or combinations thereof.

In certain aspects, a detected decrease in the level of Vitamin D-binding protein, Alpha-2-HS-glycoprotein, Hemopexin, Transthyretin, Apolipoprotein A-I, Angiotensinogen, Complement C3, Alpha-2-macroglobulin, or a combination thereof indicates that the nephrotic syndrome is steroid sensitive.

In certain aspects, a detected increase in the level of Alpha-1-acid glycoprotein, Thyroxine-binding globulin, Alpha-1-acid glycoprotein 2, Zinc-alpha-2-glycoprotein, Alpha-1B-glycoprotein, or a combination thereof, indicates that the nephrotic syndrome in the subject is steroid sensitive.

It is noted that the disclosed markers together provide greater predictive power, whatever the metric, than any one marker. The markers may be predictive in different subpopulations or the expression of two or more of the markers may be coordinated, for example, they may share a common biological presence or function. The aggregate predictive value is not necessarily additive and different combinations of the markers can provide different degrees of predictive accuracy. The statistical treatment used maximized predictive power and the marker combination was the result based on the reference populations studied. Thus, a patient sample is tested with the combination of markers, and the diagnosis, in principle, is calculated based on the combination of markers, because of the coordinated presence of two or more of the markers and the diagnostic metric based on the plurality of markers, such as one of the marker panels disclosed herein. Because of the statistic treatment, such as logistic regression, any one of the variables contributing to the multivariable metric may have a greater or lesser contribution to the maximized total. If a patient has a score, a sum and the like that is at least 30%, at least 40%, at least 50%, at least 60% or greater of the aggregated metric of the combination of markers, even in circumstances where a patient may be negative for one or more of the markers, because of being positive for some or more of the heavily weighted markers, that patient is considered more likely to have either SSNS or SRNS. The threshold score, sum and the like, which may be a reference or standard value, which may be a population mean value, and the acceptable level of patient/experimental sample similarity to that score, sum and the like to yield a positive test result, indicative of the possibility of the presence of SSNS or SRNS, is a design choice and may be determined by a statistical analysis that provides a confidence limit or level of detecting a positive sample or may be developed empirically, at the risk of a false positive. That level may be at least 30%, at least 40%, at least 50%, at least 60% or greater, of the aggregated metric of the combination of markers or the population sum, the reference value and so on. The threshold or "tolerance", that is, the degree of acceptable similarity of the patient score, sum and the like from the population score, sum and the like can be increased, that is, the patient score must be very near the population score, to increase sensitivity.

The predictive power of a marker or a panel can be measured using any of a variety of statistics, such as, specificity, sensitivity, positive predictive value, negative predictive value, diagnostic accuracy, AUC, of, for example, ROC curves which are a relationship between specificity and sensitivity, although it is known that the shape of the ROC curve is a relevant consideration of the predictive value, and so on, as known in the art.

The use of multiple markers enables a diagnostic test which is more robust and is more likely to be diagnostic in a greater population because of the greater aggregate predictive power of the plurality of markers considered together as compared to use of any one marker alone.

Different assay formats may be used. Microarrays enable simultaneous testing of multiple markers and samples. Thus, a number of controls, positive and negative, can be included in the microarray. The assay then can be run with simultaneous treatment of plural samples, such as a sample from one or more known affected patients, and one or more samples from normals, along with one or more samples to be tested and compared, the experimentals, the patient sample, the sample to be tested and so on. Including internal controls in the assay allows for normalization, calibration and standardization of signal strength within the assay. For example, each of the positive controls, negative controls and experimentals can be run in plural, and the plural samples can be a serial dilution. The control and experimental sites also can be randomly arranged on the microarray device to minimize variation due to sample site location on the testing device.

Normalized measurements of all candidate phage-expressed proteins can be independently analyzed for statistically significant differences between a patient group and normal group, for example, by t-test using JMP statistical software (SAS, Inc., Cary, N.C.). Various combinations of markers with differing levels of independent discrimination for samples tested can be statistically combined in a variety of ways. The statistical treatment is one which compares, in a multivariable analytical fashion, all of the markers in various combinations to obtain a panel of markers with maximal likelihood of being associated with the presence of disease. As in any population statistic, the selection of markers is dictated by the number and type of samples used. As such, an "optimal combination of markers" may vary from population to population or be based on the stage of the anomaly, for example. An optimal combination of markers may be altered when tested in a large sample set (>1000) based on variability that may not be apparent in smaller sample sizes (<100) or may demonstrate reduced deviation because of validation of population prevalence of the marker. Weighted logistic regression is a logical approach to combining markers with greater and lesser independent predictive value. An optimal combination of markers for discriminating the samples tested can be defined by organizing and analyzing the data using ROC curves, for example.

The panels (combined measures of two or more markers) disclosed herein for the identification of SSNS or SRNS are believed to have a high combined predictive value and demonstrate discrimination between SSNS and SRNS. A panel may comprise at least two markers; at least three markers; at least four markers; at least five markers; at least six markers; at least seven markers; at least eight markers; at least nine markers; at least ten markers and so on, the number of markers governed by the statistical analysis to obtain maximal predictability of outcomes. Thus, for example, the examples and panels described herein are examples only.

The predictive power of a marker or a panel can be measured using any of a variety of statistics, such as, specificity, sensitivity, positive predictive value, negative predictive value, diagnostic accuracy, AUC, of, for example, ROC curves which are a relationship between specificity and sensitivity, although it is known that the shape of the ROC curve is a relevant consideration of the predictive value, and so on, as known in the art.

The use of multiple markers enables a diagnostic test which is more robust and is more likely to be diagnostic in a greater population because of the greater aggregate predictive power of the plurality of markers considered together as compared to use of any one marker alone.

The data presented herein clearly demonstrate a molecular signature in peripheral blood with ability to distinguish SSNS and/or SRNS, wherein the full panel provides the most accurate diagnosis of SSNS and/or SRNS. Partial panels such as three-, four- or five-gene panels may be used.

In one aspect, a computerized, i.e., computer-implemented, method for diagnosis of SSNS and/or SRNS in an individual is disclosed, comprising analyzing, using a processor, an expression profile representing the normalized expression levels of genes in a blood sample of said individual by subjecting the expression profile to a formula based on a statistical analysis of known expression profiles, the known expression profiles representing the normalized expression level of each one of said genes in SSNS and/or SRNS patients and in control individuals, thereby obtaining a value corresponding to the probability that the tested individual has SSNS and/or SRNS.

In certain aspects, the expression profile representing the normalized expression levels of the genes in the blood sample of the tested individual is obtained by measuring, i.e., determining, the expression levels of said genes in said blood sample and normalizing the expression levels measured.

In certain aspects, the value obtained following applying said formula to said expression profile is compared with a predetermined cut-off value, and said value being higher than said cut-off value indicates that the tested individual has SSNS and/or SRNS.

Measuring expression levels for each one of the genes can be carried out using a variety of methods known in the art for detection and quantitating of gene products such as, without being limited to, those disclosed in detail in the experimental section hereinafter. The term "gene product" as used herein refers to the expression product, which may be either the direct transcript of the gene, i.e., an RNA such as mRNA, tRNA, or any other type of RNA, or a protein encoded by translation of a mRNA. RNA levels can be measured by appropriate methods such as nucleic acid probe microarrays, Northern blots, RNase protection assays (RPA), quantitative reverse-transcription PCR (RT-PCR), dot blot assays and in-situ hybridization. Alternatively, protein levels can be measured using methods based on detection by antibodies. Accordingly, the expression level of each one of the genes measured according to the methods of the present invention is, in fact, the measured level of a product expressed by each one of said genes, wherein said product may be either a protein expressed by said gene or RNA transcribed from said gene, or both.

In certain embodiments, the expression level, more particularly the amount of gene transcript, of each one of the genes is determined, i.e., quantitated, using a nucleic acid probe array. Such nucleic acid probe arrays can be of different types and may include probes of varying types such as, e.g., short-length synthetic probes (20-mer or 25-mer), full length cDNA or fragments of gene, amplified DNA, fragments of DNA (generated, e.g., by restriction enzymes) and reverse transcribed DNA. The nucleic acid probe array may be a custom array, including probes that hybridize to particular preselected subsequences of mRNA gene sequences of the genes or amplification products thereof, or a generic array designed to analyze mRNAs irrespective of sequence.

In methods using a nucleic acid probe array, nucleic acids obtained from a test blood sample are usually reverse-transcribed into labeled cDNA, although labeled mRNA can be used directly. The sample containing the labeled nucleic acids is then contacted with the probes of the array, and upon hybridization of the labeled nucleic acids that are related to the tested genes to the probes, the array is typically subjected to one or more high stringency washes to remove unbound nucleic acids and to minimize nonspecific binding to the nucleic acid probes of the arrays. Binding of labeled nucleic acid is detected using any of a variety of commercially available scanners and accompanying software programs. For example, if the nucleic acids from the sample are labeled with a fluorescent label, hybridization intensity can be determined by, e.g., a scanning confocal microscope in photon counting mode. The label can provide a signal that can be amplified by enzymatic methods, or other labels can be used including, e.g., radioisotopes, chromophores, magnetic particles and electron dense particles.

Those locations on the probe array that are hybridized to labeled nucleic acid are detected using a reader as commercially available. For customized arrays, the hybridization pattern can then be analyzed to determine the presence and/or relative or absolute amounts of known mRNA species in the sample being analyzed.

In other aspects, the expression levels, more particularly the gene transcript, of each one of the genes may be quantitated using a real time reverse-transcription PCR (real time RT-PCR) method, as exemplified herein. These methods involve measurement of the amount of amplification product formed during an amplification process, e.g., by a fluorogenic nuclease assay, to detect and quantitate specific transcripts of the genes of interest. These assays continuously measure PCR product accumulation using a dual-labeled fluorogenic oligonucleotide probe as in the approach frequently referred to in the literature simply as the TaqMan® method.

In further embodiments, the expression level, more particularly the amount of gene transcript, of each one of the genes is quantitated using a dot blot assay and in-situ hybridization. In such assays, a blood sample from the tested individual is spotted on a support, e.g., a filter, and then probed with labeled nucleic acid probes that specifically hybridize with nucleic acids derived from one or more of the genes the expression level of which is measured. After hybridization of the probes with the immobilized nucleic acids on the filter, unbound nucleic acids are rinsed away and the presence of hybridization complexes is detected and quantitated on the basis of the amount of labeled probe bound to the filter.

In certain embodiments, the gene product the level of which is measured is a protein that can be detected by an antibody or a fragment thereof, capable of binding to that protein. The antibody or fragment thereof may be detectably labeled with any appropriate marker, e.g., a radioisotope, an enzyme, a fluorescent label, a paramagnetic label, or a free radical.

According to the methods of the present invention, normalization of the expression levels measured for each one of the genes may be carried out by correcting the measured expression level of each one of said genes by the expression level of at least one control, i.e., reference, gene whose expression in blood is relatively stable. In certain embodiments, normalization of the expression levels measured for each one of the genes is carried out by dividing the expression level measured for each of said genes by the geometric mean of the expression levels of more than one, i.e., two, three, four or more, control genes.

The known expression profiles disclosed may be predetermined expression profiles representing the normalized expression level of each one of the genes measured in patients suspected of having SSNS and/or SRNS and/or in control individuals. A statistical analysis may be applied to these predetermined expression profiles, using a processor, so as to generate a formula, which can then be applied to the expression profile established representing the normalized expression level of each one of the genes for the tested individual. The end result of subjecting to that formula the expression profile of the tested individual is a value between 0 and 1 corresponding to the probability that said individual has SSNS and/or SRNS, which is compared to a cut-off value to determine a positive or negative diagnosis.

The term "processor", as used herein, refers to a logic circuitry that responds to and processes the basic instructions that drive a computer system. A processor may also be implemented as a microprocessor, microcontroller, application specific integrated circuit (ASIC) or discrete logic.

The statistical analysis applied to the predetermined expression profiles in order to generate the formula can be based on any suitable statistical model. In certain embodiments, the statistical model is a general linear model, such as a logistic regression model or classification trees. According to a more particular embodiment, the statistical model is a logistic regression model.

In particular embodiments, the statistical model is a logistic regression model, and the expression profile representing the normalized expression level of each one of the genes whose expression levels are measured for the tested individual is subjected to the formula $P=e^N/(1+e^N)$, wherein N represents the weighted sum of the natural logarithms of the normalized expression levels of said genes, with the addition of a constant, calculated by summing the natural logarithms of all of the normalized expression levels included in the expression profile established, each multiplied by a predetermined regression coefficient value, and adding a predetermined constant value; and P is a value between 0 and 1 corresponding to the probability that the tested individual has SSNS and/or SRNS. It should be noted that the predetermined regression coefficient values used to multiply the natural logarithm of each one of the normalized expression levels included in the expression profile established, as well as the predetermined constant added, are determined by the statistical analysis used so as to generate the formula.

In one aspect, a method of determining whether a subject has SSNS or SRNS is disclosed. The method may comprise the step of determining the level of one or more markers in a biofluid; wherein the biomarker indicates a level of a protein selected from Vitamin D-binding protein, Alpha-2-HS-glycoprotein, Hemopexin, Transthyretin, Apolipoprotein A-I, Angiotensinogen, Complement C3, Alpha-2-macroglobulin, Alpha-1-acid glycoprotein, Thyroxine-binding globulin, Alpha-1-acid glycoprotein 2, Zinc-alpha-2-glycoprotein, Alpha-1B-glycoprotein, or combinations thereof. In one aspect, the method may comprise the step of determining the level of each marker in a panel, wherein the panel comprises at least two, or at least three, or at least four, or at least five, or at least six, or all of the markers selected from VDBP, NGAL, FetuinA, AGP1, AGP2, A2MCG, and Prealbumin.

In one aspect, where an increase in the level of one or more of Alpha-1-acid glycoprotein, Thyroxine-binding globulin, Alpha-1-acid glycoprotein 2, Zinc-alpha-2-glycoprotein, Alpha-1B-glycoprotein, or a combination thereof in said subject is detected, the subject is determined to have steroid sensitive nephrotic syndrome, and is treated accordingly.

In one aspect, where a decrease in the level of one or more of Vitamin D-binding protein, Alpha-2-HS-glycoprotein, Hemopexin, Transthyretin, Apolipoprotein A-I, Angiotensinogen, Complement C3, Alpha-2-macroglobulin, or a combination thereof in said subject is detected, the subject is determined to have steroid sensitive nephrotic syndrome, and is treated accordingly.

In one aspect, the level of at least two biomarkers, or at least three biomarkers, or at least four biomarkers, or at least five biomarkers, or at least six biomarkers, or at least seven biomarkers, or at least eight biomarkers, or at least nine biomarkers, or at least ten biomarkers, or at least eleven biomarkers, or at least eleven biomarkers, or at least twelve biomarkers, or at least thirteen biomarkers is determined. Any combination of the above-described biomarkers may be used.

In one aspect, the level of one or more biomarkers may be determined by measurement of a protein product of said biomarker.

In one aspect, the level of one or more biomarkers may be determined by measurement of mRNA expression of said biomarker.

In one aspect, the level of the biomarker is compared to a control. The control may be readily determined by one of ordinary skill in the art, and may include, for example the known level of a particular biomarker as exists in a population that does not have nephrotic syndrome.

In one aspect, the biomarker may be compared to a control, and the biomarker expression may be normalized to the expression of a gene that is known to be unchanged in nephrotic syndrome (i.e., a housekeeping gene).

In one aspect, the biofluid is urine. Other biofluids or biological samples such as tissue samples may also be used.

In one aspect, the biomarker may be selected from mRNA, and protein.

In one aspect, at least seven markers are assayed, and wherein all seven markers have a predictive value of greater than or equal to about 0.50 AUC for detecting SSNS. In a further aspect, at least five or at least six markers are assayed, and the at least five or at least six markers have a predictive value of greater than or equal to about 0.60 AUC for detecting SSNS. In one aspect, at least four markers are assayed, and the at least four markers have a predictive value of greater than or equal to about 0.70 AUC for detecting SSNS. In one aspect, at least one marker is assayed, the at least one marker having a predictive value of greater than or equal to about 0.90 AUC for detecting SSNS. In one aspect, at least seven markers are assayed, wherein the at least seven markers have an AUC, applying multivariate analysis, of about 0.90 for detecting SSNS.

Where a subject is determined to have steroid sensitive nephrotic syndrome, the subject may then be administered an effective amount of a suitable steroid. The particular steroid and dose may be readily determined by one of ordinary skill in the art.

Where, applying the steps set forth above, a subject is identified as having steroid resistant nephrotic syndrome, the subject may be administered an effective amount of a non-steroid based treatment. Such treatment also being readily appreciated by one of ordinary skill in the art.

Kits

In one aspect, a kit is disclosed. The kit may comprise one or more agents capable of binding to a protein of interest (a marker), wherein the protein of interest may be selected from Vitamin D-binding protein, Alpha-2-HS-glycoprotein, Hemopexin, Transthyretin, Apolipoprotein A-I, Angiotensinogen, Complement C3, Alpha-2-macroglobulin, Alpha-1-acid glycoprotein, Thyroxine-binding globulin, Alpha-1-acid glycoprotein 2, Zinc-alpha-2-glycoprotein, Alpha-1B-glycoprotein, or a combination thereof. In one aspect, the kit may comprise a panel having at least two, or at least three, or at least four, or at least five, or at least six, or all of the markers selected from VDBP, NGAL, FetuinA, AGP1, AGP2, A2MCG, and Prealbumin.

The one or more agents capable of binding to a protein of interest may comprise an antibody. The kit may comprise one or more binding agents capable of binding to at least two, or at least three, or at least four, or at least five, or at least six, or at least seven, at least eight, or at least nine, or at least ten, or at least eleven or at least twelve, or at least thirteen of the disclosed proteins of interest. Each binding agent may be independently capable of binding to one or more of Vitamin D-binding protein, Alpha-2-HS-glycoprotein, Hemopexin, Transthyretin, Apolipoprotein A-I, Angiotensinogen, Complement C3, Alpha-2-macroglobulin, Alpha-1-acid glycoprotein, Thyroxine-binding globulin, Alpha-1-acid glycoprotein 2, Zinc-alpha-2-glycoprotein, Alpha-1B-glycoprotein.

The one or more agents capable of binding to the protein of interest may comprise an oligonucleotide.

In one aspect, a substrate comprising one or more binding agents is disclosed. The one or more binding agents may have specificity for at least two, or at least three, or at least four, or at least five, or at least six, or at least seven, at least eight, or at least nine, or at least ten, or at least eleven or at least twelve, or at least thirteen proteins of interest, wherein the agent(s) capable of binding to the one or more biomarkers is/are affixed to the substrate.

In other aspects, the kit may comprise, for example, in a compartmentalized container, a plurality of binding agents specific to one or more biomarkers as described herein, and optionally, one or more binding agents specific to a control protein such as a protein expressed from a housekeeping gene. In one aspect, a diagnostic kit for determining a treatment protocol for a patient comprising the above components is disclosed. In another aspect, disclosed is the use of a diagnostic kit comprising the above components for determining a treatment protocol in a patient. In one aspect, the binding agents may comprise antibodies as understood by one of ordinary skill in the art. In a further aspect, the binding agents may comprise oligonucleotides that may be hybridizing probes for hybridization with the test genes under stringent conditions or primers suitable for PCR amplification of the test genes.

Detection Methods

Biomarker Expression May be Determined Using any Known Method.

In one aspect, the one or more biomarkers described herein may be detected using an agent that binds the polypeptide of the one or more biomarkers (e.g., the biomarker protein or an antigenic fragment thereof). For example, one may use an antibody specific to one or more biomarkers and detect biomarker expression by contacting the a biological sample from the subject, for example urine, with the antibody. In such aspects, the methods may involve providing a sample from a patient, contacting the sample with an antibody directed to one or more biomarkers, and predicting the likelihood that the patient's will respond to steroid therapy based upon binding of the antibody to the sample. In one aspect, the method may comprise predicting that the patient is likely to respond to steroids based upon binding of the antibody to the sample. In another aspect, the method may comprise predicting that the patient is unlikely to respond to steroid therapy based upon lack of binding of the antibody to the sample. In some aspects, depending on the biomarker used, the method may comprise predicting that the patient is likely or unlikely to respond to steroid therapy based on both binding and lack of binding of the antibody to the sample.

In another aspect, biomarker polynucleotides may be detected using one or more primers that hybridize with one or more polynucleotides (e.g., a biomarker mRNA, cDNA or RNA).

The disclosed biomarkers may be detected using any interaction partner that binds a biomarker protein or an antigenic fragment thereof. Thus, any entity that binds detectably to a biomarker may be utilized, so long as it binds the biomarker with an appropriate combination of affinity and specificity.

In one aspect, the detection of the biomarker may be carried out using antibodies, or fragments (e.g., F(ab) fragments, F(ab')2 fragments, Fv fragments, or sFv fragments, etc. In certain aspects, chimeric antibodies may be used, e.g., "humanized" or "veneered" antibodies as are known in the art.

When antibodies are used to detect the disclosed biomarkers, these may be prepared by any of a variety of techniques known to those of ordinary skill in the art.

It is to be understood that the present invention is not limited to using antibodies or antibody fragments as agents capable of binding one or more biomarkers as described herein. In particular, synthetic moieties that mimic the functions of antibodies may be used. Several approaches to designing and/or identifying antibody mimics have been proposed and demonstrated and are known in the art (e.g., Hsieh-Wilson et al., Acc. Chem. Res. 29:164, 2000 and Peczuh and Hamilton, Chem. Rev. 100:2479, 2000). For example, small molecules that bind protein surfaces in a fashion similar to that of natural proteins have been identified by screening synthetic libraries of small molecules or natural product isolates. Similarly, combinatorial approaches have been successfully applied to screen libraries of peptides and proteins for their ability to bind a range of proteins. Alternative protein scaffolds that are loosely based around the basic fold of antibody molecules have been suggested and may be used to detect the disclosed biomarkers. Antibody mimics comprising a scaffold of a small molecule such as 3-aminomethylbenzoic acid and a substituent consisting of a single peptide loop have also been constructed. The peptide loop performs the binding function in these mimics. A synthetic antibody mimic comprising multiple peptide loops built around a calixarene unit has also been described.

Any available strategy or system may be utilized to detect association between a biomarker and an agent designed to detect the biomarker. In certain aspects, association may be detected by using a detectable label. In other aspects, association may be detected by using a labeled secondary agent that binds specifically with the primary agent that binds to the biomarker, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Examples of indirectly detectable include chemiluminescent labels, e.g., enzymes that are capable of converting a substrate to a chromogenic product such as alkaline phosphatase, horseradish peroxidase and the like.

Once a labeled interaction partner has bound the one or more biomarker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

Association between a detection agent and the one or more biomarkers may be assayed by contacting the detection agent with a sample that includes the biomarker. Depending upon the nature of the sample, appropriate, non-limiting methods may include immunohistochemistry (IHC), radioimmunoassay, ELISA, immunoblotting and fluorescence activates cell sorting (FACS). In the case where the protein is to be detected in a tissue sample, e.g., a biopsy sample, IHC may be a particularly appropriate detection method. Techniques for obtaining tissue and cell samples and performing IHC and FACS are well known in the art.

Where large numbers of samples are to be handled (e.g., when simultaneously analyzing several samples from the same patient or samples from different patients), it may be desirable to utilize arrayed and/or automated formats. In certain embodiments, tissue arrays may be used. Tissue arrays may be constructed according to a variety of techniques. According to one procedure, a commercially-available mechanical device (e.g., the manual tissue arrayer MTA1 from Beecher Instruments of Sun Prairie, Wis.) is used to remove an 0.6-micron-diameter, full thickness "core" from a paraffin block (the donor block) prepared from each patient, and to insert the core into a separate paraffin block (the recipient block) in a designated location on a grid. In preferred embodiments, cores from as many as about 400 patients (or multiple cores from the same patient) can be inserted into a single recipient block; preferably, core-to-core spacing is approximately 1 mm. The resulting tissue array may be processed into thin sections for staining with interaction partners according to standard methods applicable to paraffin embedded material.

Whatever the format or detection strategy, identification of a discriminating titer can simplify binding studies to assess the desirability of using an interaction partner. In such studies, the interaction partner is contacted with a plurality of different samples that preferably have at least one common trait (e.g., tissue of origin), and often have multiple common traits (e.g., tissue of origin, stage, microscopic characteristics, etc.). In some cases, it will be desirable to select a group of samples with at least one common trait and at least one different trait, so that a titer is determined that distinguishes the different trait. In other cases, it may be desirable to select a group of samples with no detectable different traits, so that a titer is determined that distinguishes among previously indistinguishable samples. Those of ordinary skill in the art will understand, however, that the present invention often will allow both of these goals to be accomplished even in studies of sample collections with varying degrees of similarity and difference.

Example 1

Differential biomarkers in human urine samples that can distinguish patient in relapse with steroid resistant nephrotic syndrome (SRNS) compared to patients with Steroid Sensitive Nephrotic Syndrome (SSNS) are investigated. Samples from a cohort of ten patients in each group are prepared using a 4-plex isotope tagging method (iTRAQ) followed by nanoLC-MSMS profiling of the sample group for protein identification and evaluation of quantitative changes. Collectively over 150 proteins are identified from the sample sets. Statistical analysis of the protein changes reveal 13 protein changes with p values<0.05. Table 1 shows the average fold changes for SSNS/SRNS log 2 ratios and p-values based on t-test. Eight proteins are down in the SSNS cohort (Master N's 30, 72, 59, 21, 12, 58, 4, and 41) while five proteins were up in SSNS (Master N's 19, 38, 57, 9 and 11). The significant downregulation of Vitamin D-binding protein in the SSNS cohort is validated by ELISA assays.

TABLE 1

Average Fold Changes for SSNS/SRNS log2 Ratios and P-Values Based on T-Test

| Master N | Accession | Protein Name | SSNS/SRNS Group A | SSNS/SRNS Group B | SSNS/SRNS Group C | SSNS/SRNS Group D | SSNS/SRNS Group E | Average Log2 | p-value |
|---|---|---|---|---|---|---|---|---|---|
| 30 | sp|P02774|VTDB_HUMAN | Vitamin D-binding protein | −0.668 | −0.529 | −0.628 | −0.078 | −0.919 | −0.564 | 0.015 |
| 72 | sp|P02765|FETUA_HUMAN | Alpha-2-HS-glycoprotein | −0.530 | −0.466 | −0.365 | | −0.278 | −0.410 | 0.005 |
| 59 | sp|P02790|HEMO_HUMAN | Hemopexin | −0.328 | −0.366 | −0.337 | | −0.554 | −0.396 | 0.005 |
| 21 | sp|P02766|TTHY_HUMAN | Transthyretin | −0.281 | −0.531 | −0.326 | −0.052 | −0.491 | −0.336 | 0.017 |
| 12 | sp|P02647|APOA1_HUMAN | Apolipoprotein A-1 | −0.139 | −0.368 | −0.332 | −0.186 | −0.575 | −0.320 | 0.014 |
| 58 | sp|P01019|ANGT_HUMAN | Angiotensinogen | −0.263 | −0.256 | −0.260 | | −0.376 | −0.281 | 0.003 |
| 4 | sp|P01024|CO3_HUMAN | Complement C3 | −0.323 | −0.098 | −0.208 | −0.059 | −0.211 | −0.180 | 0.018 |
| 41 | sp|P01023|A2MG_HUMAN | Alpha-2-macroglobulin | −0.139 | −0.175 | | −0.172 | | −0.162 | 0.005 |
| 19 | sp|P02763|A1AG1_HUMAN | Alpha-1-acid glycoprotein 1 | 0.140 | 0.177 | 0.183 | 0.101 | 0.086 | 0.138 | 0.002 |
| 38 | sp|P05543|THBG_HUMAN | Thyrosine-binding globulin | 0.126 | 0.240 | 0.349 | 0.213 | 0.056 | 0.197 | 0.017 |
| 57 | sp|P19652|A1AG2_HUMAN | Alpha-1 acid glycoprotein 2 | 0.238 | 0.066 | 0.317 | 0.459 | 0.247 | 0.265 | 0.014 |
| 9 | sp|P25311|ZA2G_HUMAN | Zinc-alpha-2-glycoprotein | 0.205 | −0.013 | 0.529 | 0.437 | 0.366 | 0.305 | 0.033 |
| 11 | sp|P04217|A1BG_HUMAN | Alpha-1B-glycoprotein | 0.120 | 0.324 | 0.733 | 1.681 | 0.173 | 0.406 | 0.033 |

Example 2

Using ELISA and Nephelometric based assays in a cohort of 20 patients with SRNS and 30 patients with SSNS, markers were validated. All assays were commercially available except for Alpha 1B glycoprotein which was designed by Applicant. Of the 13 proteins found to be differentially expressed by iTRAQ, 9 of those proteins could be measured in the cohort. NGAL was also measured, as Applicant had previously shown NGAL to be able to distinguish SRNS from SSNS. The results of these measurements can be found in Table 2.

TABLE 2

Table 2. Summary of biomarkers by SSNS/SSRS

| | Mean (95% CI) | | |
|---|---|---|---|
| Var | SSRS | SSNS | p |
| VDBP | 2,519.41 (669.59, 9,479.56) | 66.25 (22.46, 195.47) | <.001 |
| Prealbumin | 20,685.39 (7,391.11, 57,891.95) | 1,649.83 (712.04, 3,822.76) | <.001 |
| NGAL | 30.77 (15.01, 63.08) | 5.57 (3.10, 10.00) | 0.001 |
| Hemopexin | 4,701.67 (1,993.48, 11,089.00) | 2,049.40 (1,017.11, 4,129.39) | 0.138 |
| FetuinA | 36,723.78 (13,878.94, 97,171.38) | 3,433.82 (1,551.44, 7,600.15) | <.001 |
| TBG | 1,136.19 (320.34, 4,029.90) | 730.91 (259.97, 2,054.98) | 0.590 |
| AGP1 | 90.97 (13.43, 616.16) | 82.89 (17.38, 395.22) | 0.940 |
| A1BG | 310.97 (146.86, 658.43) | 192.57 (104.37, 355.31) | 0.325 |
| AGP2 | 141.30 (54.38, 367.14) | 35.79 (16.41, 78.04) | 0.030 |
| A2MCG | 119.93 (40.33, 356.62) | 35.79 (14.70, 87.13) | 0.090 |

Example 3

Applicant was able to find 5 proteins that could reliably distinguish between SSNS and SRNS, namely, Vitamin D-binding protein, Prealbumin, NGAL, Fetuin A, and Alpha-1 Acid Glycoprotein 2 (AGP2). Individually, these markers had ROC AUCs ranging from 0.65-0.81, but multivariate analysis (Table 3) revealed a panel of 7 markers that yielded an impressive AUC of 0.93. The results of these measurements can be found in Table 3.

TABLE 3

Summary of AUC, sensitivity and specificity of detecting SSNS

| ROCModel | AUC (95% CI) | p | Cut off probability | Sens | SPEC |
|---|---|---|---|---|---|
| Multivariate Model | 0.93 (0.85, 1.00) | — | 0.48 | 93.3% | 80.0% |

TABLE 3-continued

Summary of AUC, sensitivity and specificity of detecting SSNS

| ROCModel | AUC (95% CI) | p | Cut off probability | Sens | SPEC |
|---|---|---|---|---|---|
| VDBP | 0.81 (0.68, 0.95) | 0.044 | 0.53 | 90.0% | 70.0% |
| NGAL | 0.78 (0.65, 0.91) | 0.016 | 0.56 | 80.0% | 65.0% |
| FetuinA | 0.78 (0.65, 0.91) | 0.012 | 0.52 | 86.7% | 65.0% |
| AGP1 | 0.55 (0.39, 0.71) | 0.000 | 0.60 | 50.0% | 65.0% |
| AGP2 | 0.65 (0.49, 0.80) | 0.000 | 0.63 | 50.0% | 75.0% |
| A2MCG | 0.64 (0.48, 0.80) | 0.001 | 0.63 | 60.0% | 70.0% |
| Prealbumin | 0.78 (0.65, 0.91) | 0.020 | 0.57 | 80.0% | 65.0% |

Example 4

The following algorithm is derived from a multivariate logistical model (MM1 see Table 3 for estimated parameters).

TABLE 4

Algorithem from the multivariate logistic model with VDBP and NGAL as predictors to diagnose SSN + (or −) (AUC = 0.84, Sensitivity = 0.87 and Specificity = 0.70).

| Step | Description | Example (suppose a patient's VDBP value = 75 and NGAL value = 10) |
|---|---|---|
| 1 | Calculate a log transfered VDBP value | The log transfered VDBP = ln(75) = 4.32 |
| 2 | Calculate a log transfered NGAL value | The log transfered NGAL = ln(10) = 2.30 |
| 3 | Calculate a VDBP logit score by multiply the log transferred VDBP value in Step 1 by 0.34 | The VDBP logit score = 4.32 × 0.34 = 1.47 |
| 4 | Calculate a NGAL logit score by multiply the log transferred NGAL value in Step 2 by 0.44 | The VDBP logit score = 230 × 0.44 = 1.01 |
| 5 | Calculate the raw logit score by adding their logit scores in Steps 3 and 4 | The raw logit score = 1.47 + 1.01 = 2.48 |
| 6 | Calculate the final logit score by substracting the raw logit score from a constant 3.56 | The final logit score = 3.56 − 2.48 = 1.08 |
| 7 | Compare the final logit score with a cut off score of 0.167, the patient is SSN positive if the final logit score >0.167 and SSN negative otherwise. | Since the final logit score >0.167, the patient is SSN positive. |

REFERENCES

1. Cattran D C, Rao P (1998) Long-term outcome in children and adults with classic focal segmental glomerulosclerosis. Am J Kidney Dis 32:72-79.
2. Hari P, Bagga A, Jindal N, Srivastava R N (2001) Treatment of focal glomerulosclerosis with pulse steroids and oral cyclophosphamide. Pediatr Nephrol 16:901-905.
3. Gipson D S, Chin H, Presler T P, Jennette C, Ferris M E, Massengill S, Gibson K, Thomas D B (2006) Differential risk of remission and ESRD in childhood FSGS. Pediatr Nephrol 21:344-349.
4. Roberti I, Vyas S (2010) Long-term outcome of children with steroid-resistant nephrotic syndrome treated with tacrolimus. Pediatr Nephrol 25:1117-1124.
5. Gipson D S, Gibson K, Gipson P E, Watkins S, Moxey-Mims M (2007) Therapeutic approach to FSGS in children. Pediatr Nephrol 22:28-36.
6. Srivastava T, Simon S D, Alon U S (1999) High incidence of focal segmental glomerulosclerosis in nephrotic syndrome of childhood. Pediatric nephrology (Berlin, Germany) 13:13-18.
7. Gulati S, Sharma A P, Sharma R K, Gupta A (1999) Changing trends of histopathology in childhood nephrotic syndrome. Am J Kidney Dis 34:646-650.
8. Bonilla-Felix M, Parra C, Dajani T, Ferris M, Swinford R D, Portman R J, Verani R (1999) Changing patterns in the histopathology of idiopathic nephrotic syndrome in children. Kidney international 55:1885-1890.
9. Smith J M, Stablein D M, Munoz R, Hebert D, McDonald R A (2007) Contributions of the Transplant Registry: The 2006 Annual Report of the North American Pediatric Renal Trials and Collaborative Studies (NAPRTCS). Pediatr Transplant 11:366-373.
10. Korbet S M (1999) Clinical picture and outcome of primary focal segmental glomerulosclerosis. pp 68-73.
11. Eddy A A, Symons J M (2003) Nephrotic syndrome in childhood. Lancet 362:629-639.
12. Gulati S, Sharma A P, Sharma R K, Gupta A, Gupta R K (2002) Do current recommendations for kidney biopsy in nephrotic syndrome need modifications? Pediatric nephrology (Berlin, Germany) 17:404-408.
13. Mishra J, Ma Q, Prada A, Mitsnefes M, Zahedi K, Yang J, Barasch J, Devarajan P (2003) Identification of neutrophil gelatinase-associated lipocalin as a novel early urinary biomarker for ischemic renal injury. J Am Soc Nephrol 14:2534-2543.
14. Mishra J, Dent C, Tarabishi R, Mitsnefes M M, Ma Q, Kelly C, Ruff S M, Zahedi K, Shao M, Bean J, Mori K, Barasch J, Devarajan P (2005) Neutrophil gelatinase-associated lipocalin (NGAL) as a biomarker for acute renal injury after cardiac surgery. Lancet 365:1231-1238.
15. Bennett M, Dent C L, Ma Q, Dastrala S, Grenier F, Workman R, Syed H, Ali S, Barasch J, Devarajan P (2008) Urine NGAL predicts severity of acute kidney injury after cardiac surgery: a prospective study. Clin J Am Soc Nephrol 3:665-673.
16. Haase M, Bellomo R, Devarajan P, Schlattmann P, Haase-Fielitz A (2009) Accuracy of Neutrophil Gelatinase-Associated Lipocalin (NGAL) in Diagnosis and Prognosis in Acute Kidney Injury: A Systematic Review and Meta-analysis. Am J Kidney Dis 54:1012-1024.
17. Bolignano D, Lacquaniti A, Coppolino G, Donato V, Campo S, Fazio M R, Nicocia G, Buemi M (2009) Neutrophil gelatinase-associated lipocalin (NGAL) and progression of chronic kidney disease. Clin J Am Soc Nephrol 4:337-344.
18. Schwartz G J, Munoz A, Schneider M F, Mak R H, Kaskel F, Warady B A, Furth S L (2009) New equations to estimate GFR in children with CKD. J Am Soc Nephrol 20:629-637.
19. (2002) K/DOQI clinical practice guidelines for chronic kidney disease: evaluation, classification, and stratification. Am J Kidney Dis 39:S1-266.
20. Hirsch R, Dent C, Pfriem H, Allen J, Beekman R H, 3rd, Ma Q, Dastrala S, Bennett M, Mitsnefes M, Devarajan P (2007) NGAL is an early predictive biomarker of contrast-induced nephropathy in children. Pediatric nephrology (Berlin, Germany) 22:2089-2095.
21. Hall 1E, Yarlagadda S G, Coca S G, Wang Z, Doshi M, Devarajan P, Han W K, Marcus R J, Parikh C R (2009) IL-18 and Urinary NGAL Predict Dialysis and Graft Recovery after Kidney Transplantation. J Am Soc Nephrol.
22. Bagshaw S M, Bennett M, Haase M, Haase-Fielitz A, Egi M, Morimatsu H, D'Amico G, Goldsmith D, Devarajan P, Bellomo R (2010) Plasma and urine neutrophil gelatinase-associated lipocalin in septic versus non-septic acute kidney injury in critical illness. Intensive care medicine 36:452-461.
23. Woroniecki R P, Orlova T N, Mendelev N, Shatat I F, Hailpern S M, Kaskel F J, Goligorsky M S, O'Riordan E (2006) Urinary proteome of steroid-sensitive and steroid-resistant idiopathic nephrotic syndrome of childhood. American journal of nephrology 26:258-267.
24. Woroniecki R P, Shatat I F, Supe K, Du Z, Kaskel F J (2008) Urinary cytokines and steroid responsiveness in idiopathic nephrotic syndrome of childhood. American journal of nephrology 28:83-90.
25. Krawczeski C D, Woo J G, Wang Y, Bennett M R, Ma Q, Devarajan P (2011) Neutrophil Gelatinase-Associated Lipocalin Concentrations Predict Development of Acute Kidney Injury in Neonates and Children after Cardiopulmonary Bypass. J Pediatr. 01:10.1016/j jpeds.2010.12.057
26. Gipson, D. S., et al., Management of Childhood Onset Nephrotic Syndrome. Pediatrics, 2009. 124(2):p. 747-757.
27. Gygi, S. P., et al., Quantitative analysis of complex protein mixtures using isotope-coded affinity tags. Nat Biotechnol, 1999. 17(10): p. 994-9.
28. Ross, P. L., et al., Multiplexed protein quantitation in *Saccharomyces cerevisiae* using amine-reactive isobaric tagging reagents. Mol Cell Proteomics, 2004. 3(12): p. 1154-69.
29. Allison, P. D. (1999), *Logistic Regression Using the SAS System: Theory and Application*, Cary, N.C.: SAS Institute Inc.
30. Cox, D. R. (1970), *The Analysis of Binary Data*, New York: Chapman & Hall.
31. Cox, D. R. and Snell, E. J. (1989), *The Analysis of Binary Data,* 2nd Edition, London: Chapman & Hall.
32. DeLong, E. R., DeLong, D. M., and Clarke-Pearson, D. L. (1988), "Comparing the Areas under Two or More Correlated Receiver Operating Characteristic Curves: A Nonparametric Approach," *Biometrics,* 44, 837-845.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of diagnosing and treating a subject having a nephrotic syndrome with either steroid resistant (SRNS) or steroid sensitive nephrotic syndrome (SSNS), comprising the step of contacting a urine sample obtained from said subject with a combination of antibodies;
    wherein said combination of antibodies comprises an antibody capable of detecting Vitamin D-binding protein (VDBP), an antibody capable of detecting Neutrophil gelatinase-associated lipocalin (NGAL), and an antibody capable of detecting Fetuin A;
    wherein said combination of antibodies is used to determine the amount of VDBP, NGAL, and Fetuin A in said urine sample;
    wherein an increase in the amount of VDBP, NGAL, and Fetuin A in said urine sample as compared to a cut-off value, indicates that said subject is steroid resistant;
    wherein a decrease in the amount of VDBP, NGAL, and Fetuin A in said urine sample as compared to a cut-off value, indicates that said subject is steroid sensitive; and
    treating said steroid resistant subject with a non-steroid based therapy or said steroid sensitive subject with a steroid based therapy.

2. The method of claim 1, wherein said combination of antibodies further comprise an antibody capable of detecting alpha-1-acid glycoprotein 2 (AGP2), wherein a decrease in AGP2 levels indicate that said patient is steroid sensitive, and an increase in AGP2 levels indicate that said patient is steroid resistant.

3. The method of claim 1, wherein said combination of antibodies further comprise an antibody capable of detecting prealbumin, wherein a decrease in prealbumin levels indicate that said patient is steroid sensitive, and an increase in prealbumin levels indicate that said patient is steroid resistant.

4. A computerized method for characterizing a subject as having either steroid resistant nephrotic syndrome (SRNS) or steroid sensitive nephrotic syndrome (SSNS), comprising analyzing, using a processor, an expression profile representing the normalized expression levels of genes in a blood sample of said individual by subjecting said expression profile to a formula based on a statistical analysis of known expression profiles, said known expression profiles representing the normalized expression level of each one of said genes in said subject and in one or more control individuals, thereby obtaining a value corresponding to the probability that the tested individual has either SRNS or SSNS, wherein said genes comprise Vitamin D-binding protein (VDBP), Neutrophil gelatinase-associated lipocalin (NGAL), and Fetuin A, wherein a detected decrease in said genes indicates that said subject has steroid sensitive nephrotic syndrome and wherein a detected increase in said genes indicates that said subject has steroid resistant steroid syndrome.

5. A kit comprising a combination of antibodies capable of binding to Vitamin D-binding protein (VDBP), Neutrophil gelatinase-associated lipocalin (NGAL), and Fetuin A.

6. The kit of claim 5, further comprising an antibody capable of detecting alpha-1-acid glycoprotein 2 (AGP2), and an antibody capable of detecting prealbumin.

7. A substrate comprising a combination of antibodies capable of binding to Vitamin D-binding protein (VDBP), Neutrophil gelatinase-associated lipocalin (NGAL), and Fetuin A.

8. The substrate of claim 7, further comprising an antibody capable of binding to albumin and an antibody capable of binding to alpha-1-acid glycoprotein 2 (AGP2).

* * * * *